United States Patent [19]
Bressler

[11] Patent Number: 5,685,719
[45] Date of Patent: Nov. 11, 1997

[54] COMPUTER ASSISTED COMMUNICATION SYSTEM FOR REHABILITATING INDIVIDUALS SUFFERING FROM SPEECH IMPAIRMENT AND MINIMAL MOBILITY IN THEIR UPPER EXTREMITIES

[75] Inventor: John Willard Bressler, Sugarland, Tex.

[73] Assignee: Frank Bressler Rehabilitation Research, Inc., Houston, Tex.

[21] Appl. No.: 372,082

[22] Filed: Jan. 13, 1995

[51] Int. Cl.⁶ .............. G09B 21/00; B62M 1/14; A47B 11/00; A47C 7/54
[52] U.S. Cl. .............. 434/112; 297/411.2; 297/DIG. 4; 108/103; 108/137; 108/140; 248/118; 280/250.1; 400/715; D6/501; D12/131; D12/133
[58] Field of Search .............. 297/38, 160, 161, 297/411.2, 411.23, 411.26, 411.32, 411.33, 411.34, 411.35, 411.36, 411.37, 411.38, DIG. 4; 108/103, 102, 137, 139, 140; 248/118, 118.1, 118.3, 118.5; D12/131, 133; D6/501, 341; 434/112, 113, 227; 400/715; 280/250.1; 482/904

[56] References Cited

U.S. PATENT DOCUMENTS

| | | |
|---|---|---|
| 607,675 | 7/1898 | Barr . |
| 794,042 | 7/1905 | O'Connor . |
| 3,101,568 | 8/1963 | Tratt . |
| 4,045,011 | 8/1977 | Ford . |
| 4,069,995 | 1/1978 | Miller .............. 248/118.1 |
| 4,277,102 | 7/1981 | Aaras et al. . |
| 4,561,619 | 12/1985 | Robillard et al. . |
| 4,632,451 | 12/1986 | Lee . |
| 4,659,048 | 4/1987 | Fahrion . |
| 4,784,120 | 11/1988 | Thomas . |
| 4,996,977 | 3/1991 | Tiedeken . |
| 5,056,743 | 10/1991 | Zwar et al. . |
| 5,058,840 | 10/1991 | Moss et al. . |
| 5,072,905 | 12/1991 | Hyatt . |
| 5,108,057 | 4/1992 | Dandy, III et al. . |
| 5,120,010 | 6/1992 | Magee . |
| 5,149,033 | 9/1992 | Burzler . |
| 5,161,760 | 11/1992 | Terbrack . |
| 5,174,224 | 12/1992 | Nagy et al. .............. 108/114 |
| 5,201,485 | 4/1993 | Moss et al. . |
| 5,215,282 | 6/1993 | Bonutti . |
| 5,231,998 | 8/1993 | Rosen et al. . |
| 5,242,180 | 9/1993 | Bergeron . |
| 5,265,835 | 11/1993 | Nash . |
| 5,281,001 | 1/1994 | Bergsten et al. .............. 297/411.24 |
| 5,288,042 | 2/1994 | Grimm . |
| 5,454,581 | 10/1995 | Ringer .............. 280/304.1 |

Primary Examiner—Richard J. Apley
Assistant Examiner—John Rovnak
Attorney, Agent, or Firm—Lowe, Price, LeBlanc & Becker

[57] ABSTRACT

A system for rehabilitating a speech impaired individual confined to a wheelchair is disclosed. The system utilizes an arm movement actuator attachment which is secured to the arm rest structure of the wheelchair through a rotatable arm support platform mounted on juxtaposed, upper and lower slide rod assemblies providing X- and Y-axis movement for the rotatable platform. The platform is configured to fully support the individual's forearm and elbow to enable the individual suffering from minimal upper extremity mobility to physically contact a touch screen for enablement of interaction with a computer to communicate and therefore socialize with others.

12 Claims, 7 Drawing Sheets

COMPUTER ASSISTED COMMUNICATION SYSTEM FOR REHABILITATING INDIVIDUALS SUFFERING FROM SPEECH IMPAIRMENT AND MINIMAL MOBILITY IN THEIR UPPER EXTREMITIES

TECHNICAL FIELD

This invention relates generally to attachments for wheelchairs and, more particularly, to assisting individuals, suffering from traumatic brain injury and confined to wheelchairs, in interacting with a computer assisted system for the purpose of communicating with third parties.

BACKGROUND ART

Individuals suffering from traumatic brain injury, which can occur as a result of involvement in severe vehicular (e.g., automobile) and other types of accidents, are usually confined to wheelchairs as a result of minimal mobility in their upper and lower extremities. In addition, such individuals often lose their ability to verbally communicate and require a program of rehabilitation to relearn at least some of these skills.

Appropriate rehabilitative programs are often predicated on mastering the physical and cognitive skills necessary to enable the individual to interact with a computer by manipulating a keyboard, for example, which actuates speech and audio circuitry. This physical interaction requires the individual to move their arms and digits sufficient to access appropriate keyboard and other types of switch inputs to generate the necessary commands. Since such individuals suffer from minimal mobility in their arms, it is critical that an appropriate means of physical support be provided to break and/or lessen tone so that the individual can increase their range of motion.

In the past, air balls were positioned under the individual's arms as a means of support. The air balls prevent the upper muscles in the individual's arms from pulling down and back into a fetal position. However, various problems result through the use of air balls as a support means. For example, the air ball must be repositioned continuously to maintain effective use. Because of tone, the individual's arm has a tendency to always sink down into the ball which then causes the ball to roll. When this occurs, the individual may not have the ability to pull their arm back. Further, if the ball rolls to the right, the individual's arm would fall off the ball. If the ball rolled to the left, the individual's arm was pulled down and in towards the body.

The use of ball bearing feeders are also known for providing upper arm support but do not provide sufficient arm support.

It is accordingly one object of the present invention to rehabilitate an individual confined to a wheelchair and suffering from a speech impairment as well as minimal mobility in their upper and lower extremities, by teaching the said individual to learn to communicate.

Another object of the invention is to enable individuals suffering from traumatic brain injury to learn a computer assisted means of communication and to eventually relearn the skill of verbal communication.

Another object is to enable an individual suffering from traumatic brain injury to master the physical and cognitive skills necessary to enable them to interact with a computer for the purpose of communication and thus be able to socialize on some level.

Still a further object is to teach such an individual to increase their range of mobility in their upper extremities by appropriately supporting their forearm and elbow so that they do not have to concentrate on overcoming resistance to movement of their upper extremities within a horizontal plane.

SUMMARY OF THE INVENTION

A system for rehabilitating an individual suffering from a speech impairment and having only minimal mobility in their upper extremities is disclosed. The system according to a preferred embodiment of the invention comprises a platform having an upwardly directed surface for directly supporting at least an elbow and a forearm portion of the individual's arm. The platform is moveable with respect to a support surface. A touch screen is mounted adjacent the platform and is connected to a computer operating at least one of verbal communication and visual communication software so as to generate at least one of audibly and visually detectable information corresponding to indicia on the touch screen as actuated by the individual's hand as a result of platform movement by the individual.

The platform is preferably connected to a support surface through a pair of upper and lower slide assemblies respectively providing movement of the platform in one of X and Y coordinate directions primarily as a result of movement of the individual's arm through self bending of the elbow directly supported on the platform and in contact therewith.

The lower slide assembly is preferably attached at one end thereof to an armrest structure of a wheelchair in which the individual is confined. The opposite end of the lower slide assembly, cantilevered with respect to the end supported on the arm rest attachment, is preferably supported on a table top which is mounted to the wheelchair armrests. In this manner, smooth sliding operation of the lower slide assembly is assured to prevent the platform from jamming.

In accordance with another feature of the invention, the platform is preferably rotatably mounted relative to the upper slide assembly to assist the individual in increasing their range of upper extremity motion.

The dimensions of the moveable arm support platform may be adapted to meet the size requirements of the user. However, it is important that the upwardly directed platform surface be of sufficient size to contact and directly support both the elbow and forearm. To perform the above mentioned intended functions, the X-axis slide assembly is preferably dimensioned so as to be long enough to allow full travel of the user's arm in left and right handed directions of movement from a position of −30°−+30° relative to a vertical (Y-Z) plane extending forwardly from the user. The Y-axis slide assembly is long enough to allow full outward and inward travelling movement of the arm from a fully drawn back position at 180° to a fully extended position at 0°. The platform is preferably capable of full 360° rotation about a vertical axis so as to allow the arm to bend from a position of −30°−+90° when built as a left side support, and from a position of −90°−+30° when built as a right side support. Finally, the arm should be free to bend along the Z-axis upward from a position of +0° (flat on the platform) through +135° (i.e., up to the individual's shoulder). Therefore, there should be no limitation on upward bending or movement placed on the arm by the device of the invention.

The present invention is also directed to an attachment for a wheelchair or the like of the type having an armrest structure on each side thereof. The attachment comprises a platform having an upwardly directed surface dimensioned for directly supporting at least an elbow and a forearm of an individual seated in the wheelchair. The attachment further includes moving means, connected to a support surface on the wheelchair, for permitting movement of the platform in X and Y coordinate directions defining a plane of movement in response to movement of said individual's arm and bending of said elbow on said platform.

The present invention is also concerned with a method of rehabilitating an individual confined to a wheelchair and having minimal mobility in their upper extremities. The method of the invention comprises the steps of placing the forearm and elbow of at least one of the individual's arms on a moveable, upwardly directed support surface which is capable of virtually frictionless movement along two orthogonal coordinate axis. The individual is then taught to bend the elbow which is directly supported on the platform in order to move the platform.

Still other objects and advantages of the present invention will become readily apparent to those skilled in this art from the following detailed description, wherein only the preferred embodiments of the invention are shown and described, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BEST MODE FOR CARRYING OUT THE INVENTION

Figure 3A:
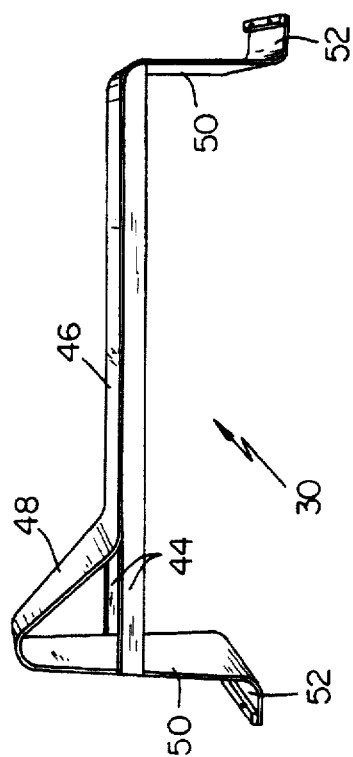
FIG. 3A is a side elevational view of a mounting assembly for use in mounting the preferred embodiment of the preferred invention to the wheelchair.
Figure 3:
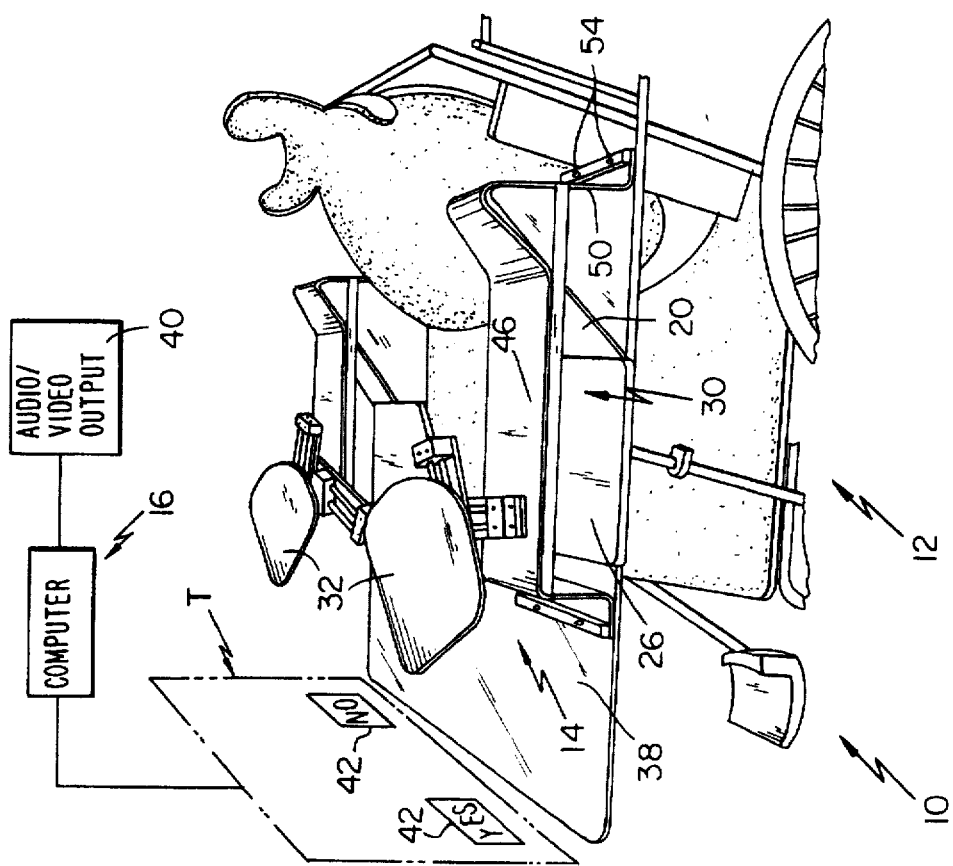
FIG. 3 is a side perspective view of the wheelchair and preferred embodiment of FIG. 2.
Figure 4:
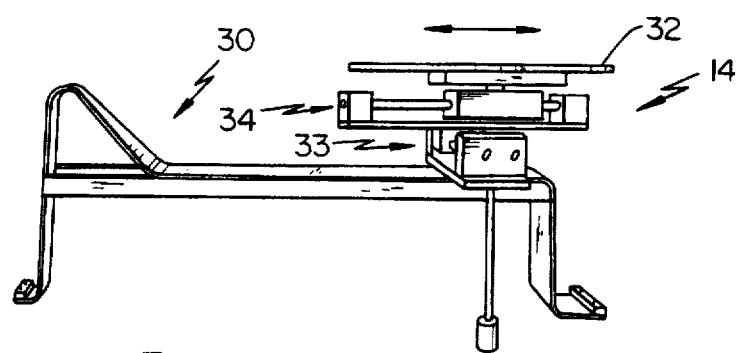
FIG. 4 is a side perspective view of an arm movement actuator attachment of the preferred embodiment of the invention.

The present invention features a system, generally designated by reference numeral 10 in FIG. 3, for rehabilitating individuals suffering from both speech impairment as well as minimal mobility in their upper extremities. These disabilities often result in individuals suffering from traumatic brain injury as may occur following involvement in a severe vehicular or other type of accident. Such individuals are usually confined to a wheelchair 12 and a prominent feature of the invention is an attachment 14 for wheelchair 12 or the like which will both support the upper extremities of the wheelchair occupant while providing same with the capability of virtually frictionless movement in a horizontal plane as actuated by the occupant's arm to enable interaction with a computer 16 for the purpose of communication and socialization at some level.

Figure 1:
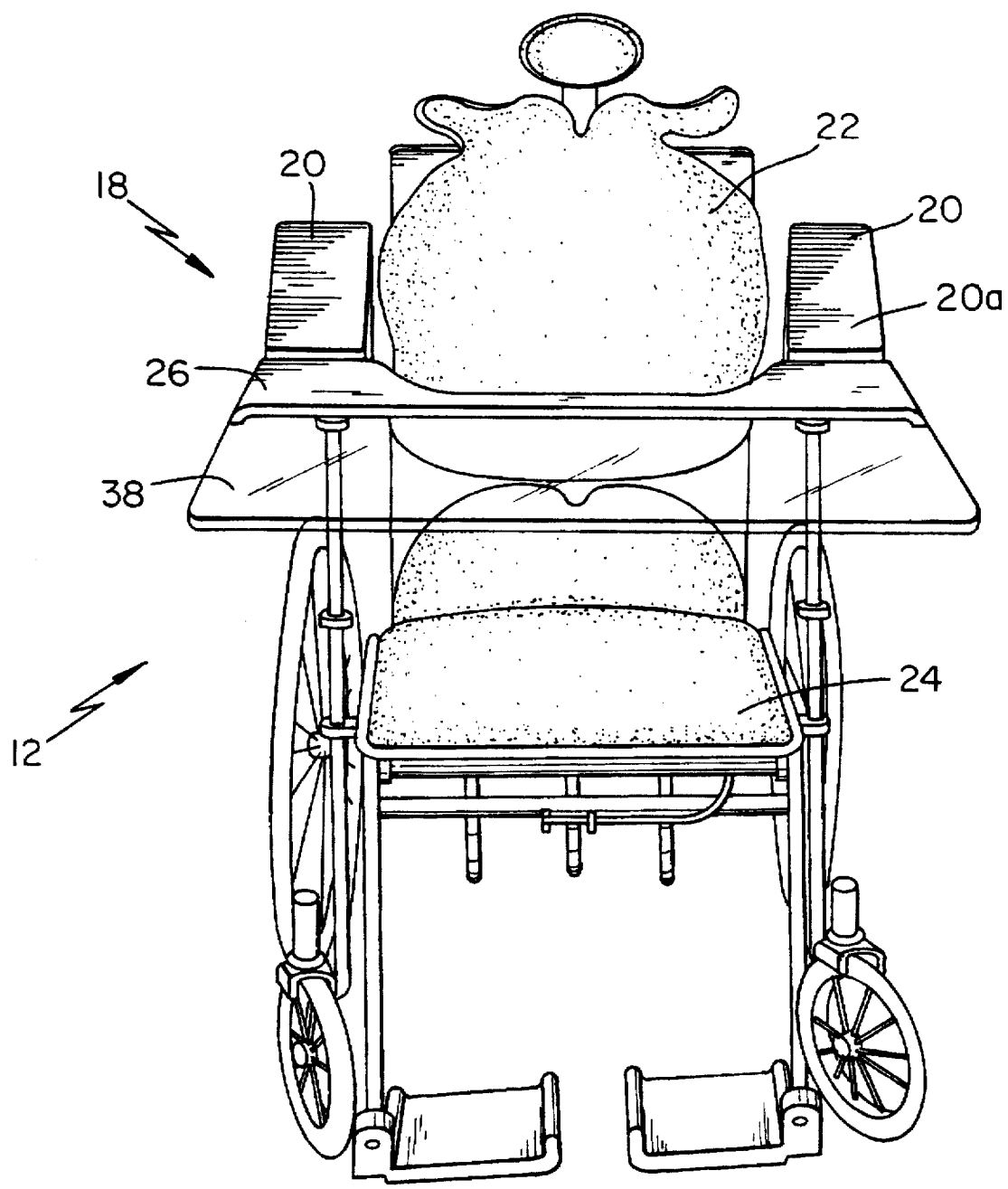
FIG. 1 is a perspective view of a wheelchair to which a preferred embodiment of the invention may be secured.

FIG. 1 is an illustration of a wheelchair 12 which may be utilized in connection with the arm movement actuator 14 of the present invention. Wheelchair 12 is shown herein for the purpose of illustrating a typical wheelchair and typical arm rest structure 18 with which the actuator attachment 14 of the invention may be advantageously used. It is to be understood, however, that the attachment 14 of the invention may also be used with other types of wheelchairs and other types of arm rest structures without departing from the spirit and scope of the invention as will be evident to one of ordinary skill in the art.

The arm rest structure 18 of the wheelchair 12 may be in the form of a pair of inclined armrests 20 respectively located on opposite sides of the wheelchair seat back 22 in elevated position above the seat 24. These armrests 20 respectively have an upper surface 20a which is forwardly and downwardly inclined to function as upper arm supports for the wheelchair occupant during normal use. As the term is used in this specification, 'forwardly' or 'longitudinally' are with reference to the forward line of sight (Y-axis) of the wheelchair occupant when normally seated in wheelchair 12.

The term 'rearwardly' means in a direction back towards the seatback 22 from a point forwardly thereof. 'Downwardly' means in the direction of the wheelchair seat 24 (Z-axis) from a point thereabove. The terms 'upper' and 'lower' are also with reference to a vertical distance from the wheelchair seat 24.

The conventional wheelchair 12 may further include a tabletop 26 extending forwardly from the inclined arm supports 20 and across the full width of the wheelchair to provide a horizontal surface in front of the wheelchair occupant for a variety of purposes.

Each arm movement actuator 14 is mounted to a stationary mounting base assembly 30 that is in turn fixedly mounted to extend forwardly from and above the inclined arm supports 20 (see, e.g., FIG. 3), in substantially vertical alignment with the associated arm support 20 and in forwardly spaced relation thereto so as to be juxtaposed, in a neutral position, above a forward or front corner of the stationary tabletop 26. Each actuator attachment 14 further includes a moveable arm support platform 32 which is mounted to the forward end of the associated mounting base assembly 30 for movement in a horizontal plane along a pair of juxtaposed, lower and upper slide rail assemblies 33 and 34 providing movement in generally X and Y coordinate directions, respectively. In the preferred embodiment, the X direction is along the width of the wheelchair 12 while the Y direction is along the longitudinal axis, i.e., in forward and rearward directions. The moveable arm support platform 34 is rotatably secured to the upper slide assembly 34 to provide for relative rotational movement of the platform about a vertical axis independent of sliding movement in the X or Y directions.

In the preferred embodiment, a touch screen T, schematically depicted in phantom line in FIG. 3, is mounted to project vertically above a horizontal tabletop extension 38 which is mounted to the front edge of the wheelchair tabletop 26 to project forwardly therefrom. This tabletop extension 38 also provides cantilevered support for each lower slide assembly 32 as discussed, infra. Touch screen T is connected to computer 16 having an operating system capable of running verbal communication software for generating at least one of visually and audibly detectable information 40 corresponding to indicia 42 on the touch screen T to enable the wheelchair occupant to verbally communicate with third parties.

The occupant, by positioning of their elbow and forearm on the upwardly directed horizontal surface of the arm support platform 32, is provided with the necessary range of virtually frictionless (i.e., approximately zero percent resistance) range of motion to touch appropriate indicia 42 geographically situated on the touch screen T to solicit the desired computer generated sound or visually displayed indicia necessary to allow the occupant to communicate with third parties.

The left and right handed arm actuator attachments 14 are preferably identical in construction and operation and will now be described hereunder with reference to FIGS. 3–7 depicting one of the actuator attachments. With reference to FIGS. 3 and 3A, each mounting base assembly 30 which supports one of actuator attachments 14 is comprised of a pair of laterally spaced support bars 44 supporting a planer sheet metal member 46 extending between the support bars between forward and rearward ends thereof. The rearward inclined portion 48 of the sheet metal 46 has the same angular inclination as the upper portion of the inclined upper arm support 20 to allow same to interfit between the rear ends of the support bars 44 as best depicted in FIG. 3. Opposite ends of the sheet metal support 46 project vertically downward from the front and rear ends of the support bars 44 to define uprights 50 which are respectively formed at their bottom edges with a mounting flange 52 for securing the mounting base assembly 30 to the armrest 20 and table top extension 38 with screws 54.

Other mounting base assembly constructions are within the scope of this invention in order to provide a stationary support bracket function for locating arm actuators 14 at the proper heights and forward location for successful operation.

Figure 2:
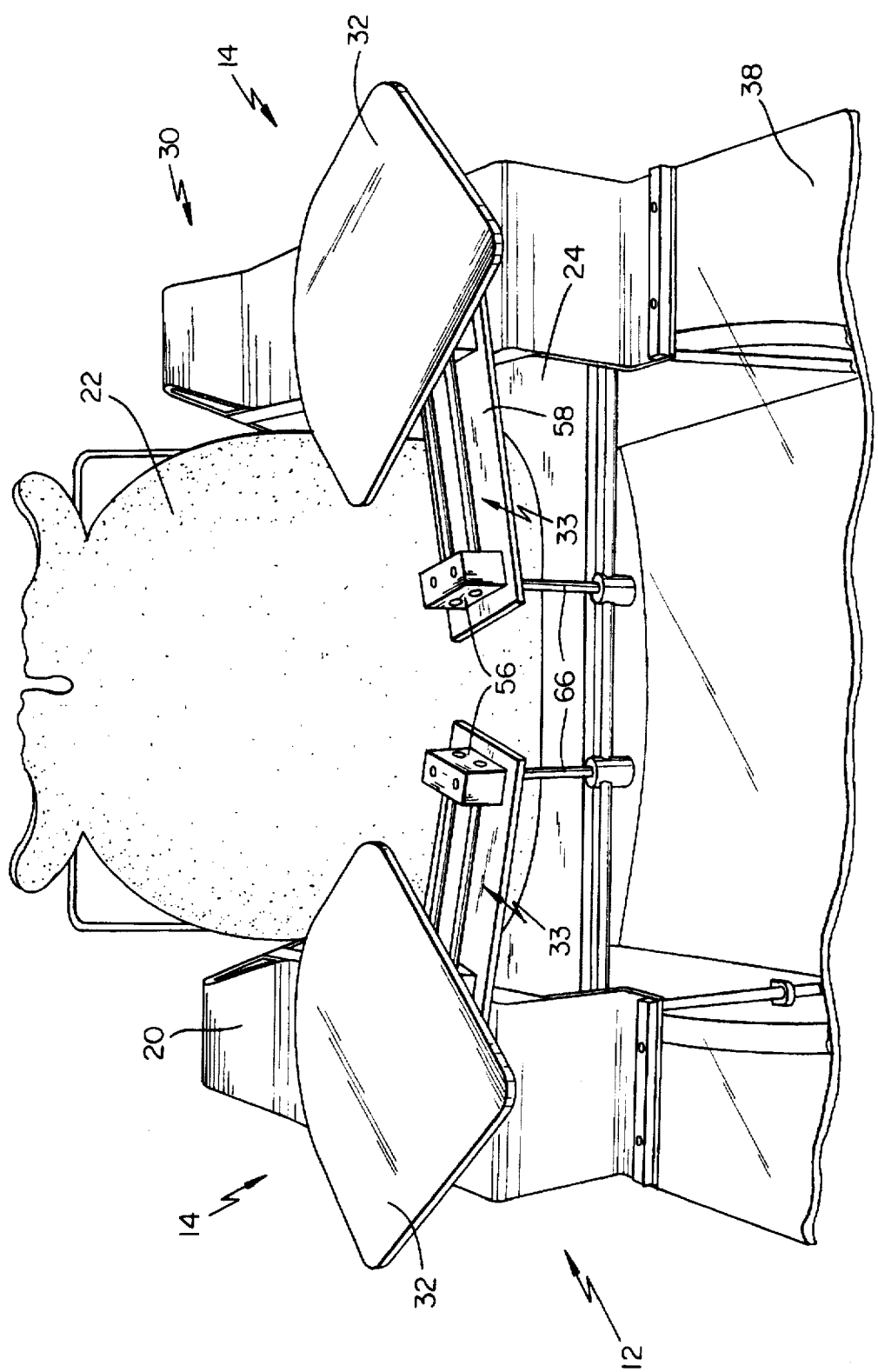
FIG. 2 is a perspective view of the wheelchair of FIG. 1 to which the preferred embodiment of the invention has been secured.
Figure 5:
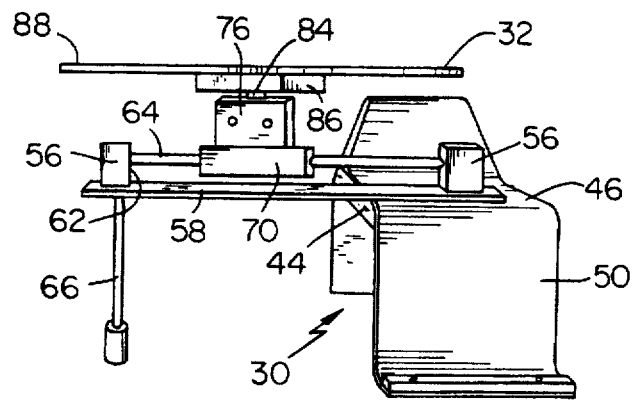
FIG. 5 is a front perspective view of the arm movement actuator attachment of the invention depicted in FIG. 4.
Figure 6:
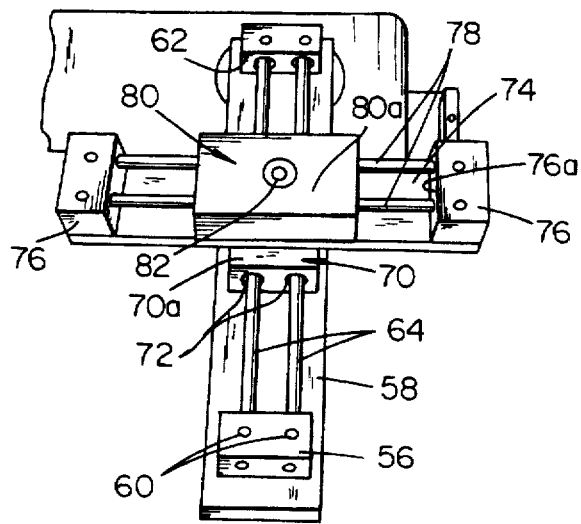
FIG. 6 is a perspective view of upper and lower slide rod assemblies of the preferred embodiment.

Each actuator attachment 14 includes lower slide rail assembly 32 extending generally in the X direction as best depicted in FIG. 2, to provide smooth X-directional sliding movement. With particular reference to FIGS. 5 and 6, each lower slide rail assembly 33 is comprised of a pair of slide rod mounting blocks 56 mounted to opposite ends of a lower slide rail mounting plate 58 of elongate, rectangular construction. The slide rod mounting blocks 56 are preferably secured to the mounting plate 58 with screws 60. Each block 56 has a vertical face 62 formed with a pair of horizontally spaced blind bores (not shown) adapted to receive ends of a pair of slide rods 64 so that the rods extend parallel to each other in space relation. One end of the lower slide rail mounting plate 58 is screwed to the forward end portion of the associated mounting base assembly 30. The other end of the lower slide rail mounting plate 58 projects inwardly in the direction of the opposite mounting assembly (i.e., in generally the X direction) and terminates in elevated position above a center portion of the tabletop extension 38 (see FIG. 2). Cantilevered support for this elevated, inner extent of slide rod assembly 33 is advantageously provided by a vertical support rod 66 which may be threadedly secured to the bottom surface of the mounting plate 58 to cooperate with the mounting base assembly 30 in providing a horizontal support base for the slide rail assemblies 33,34 as best depicted in FIG. 5.

A lower slide block 70 of preferably rectangular configuration is formed with a pair of parallel, spaced through bores 72 (FIG. 6) through which lower slide rods 64 respectively extend to define a horizontal slide path for the lower slide block in the X direction. Preferably, the lower slide block 70 may travel along the full length of the lower slide rods 64. Roller bearings (not shown in detail) are preferably located within the through bores 72 to provide virtually frictionless movement of the lower slide block 70 along the lower slide rods 64.

The lower slide block 70 has an upwardly directed horizontal flat surface 70a to which is bolted an upper slide rod connecting plate 74 adapted to extend horizontally in the Y direction, as best depicted in FIG. 6. Upper connecting plate 74 is also of elongate, rectangular construction and a pair of upper slide blocks 76 are screwed or otherwise attached to opposite ends of this connecting plate. Vertical, inward facing surfaces 76a of the upper slide blocks 76 are also formed with horizontally spaced blind bores (not shown in detail) adapted to receive opposite ends of a pair of upper slide rods 78 which define a slide path in the Y direction, extending orthogonal to the lower slide path in the X direction defined by the lower slide rods 64. An upper slide block 80 is mounted for sliding movement in the Y direction by virtue of a pair of horizontally spaced through bores receiving the upper slide rods 78, respectively. These through bores may also be equipped with roller bearings to provide virtually frictionless smooth sliding movement of the upper slide block 80 in the Y direction.

Figure 7:
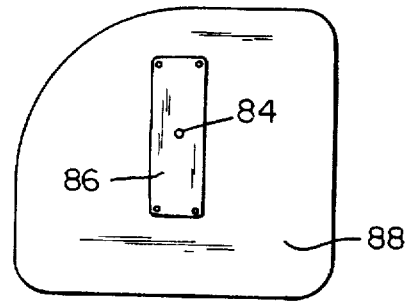
FIG. 7 is a plan view of a platform supporting plate of the preferred embodiment when viewed from the lower surface thereof.

The upper slide block 80 has an upwardly directed flat surface 80a formed with a vertical bore 82 adapted to receive a pivot pin 84 which projects downwardly from a mounting block 86 secured to a lower surface of a platform supporting plate 88 as best depicted in FIG. 7. This platform supporting plate 88 is secured to arm support platform 32 to provide rigid support. By virtue of this pin connection, the arm support platform 32 is capable of rotational movement through 360° about a vertical axis relative to the upper slide block 80.

Figure 8A:
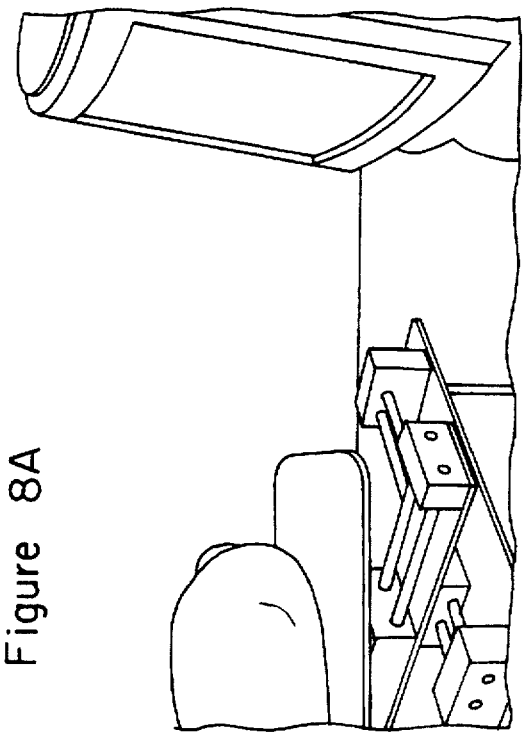
FIGS. 8A–8K are perspective views of the preferred embodiment to depict the manner in which the invention supports a wheelchair ridden individual's elbow and forearm.
Figure 8B:
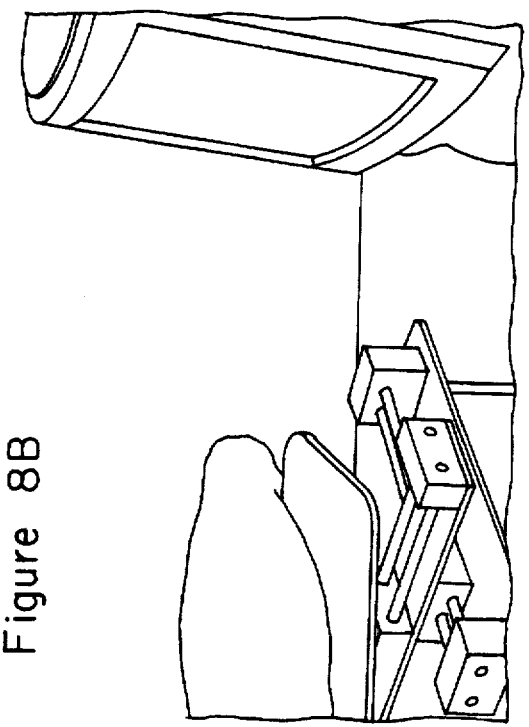
Figure 8C:
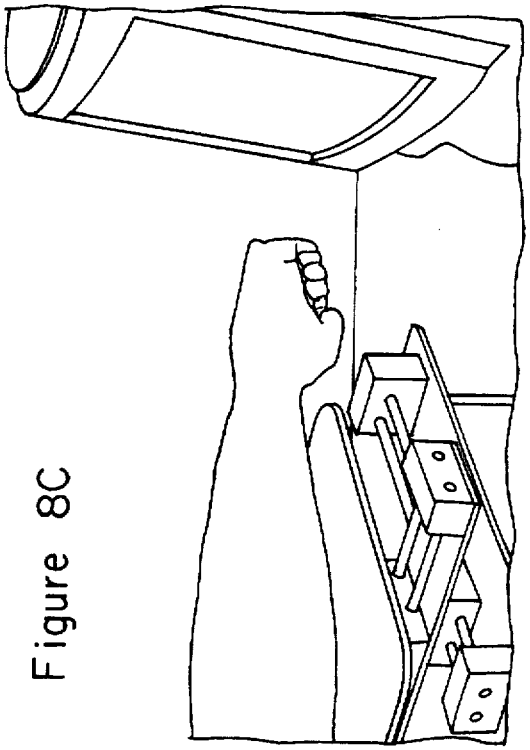
Figure 8D:
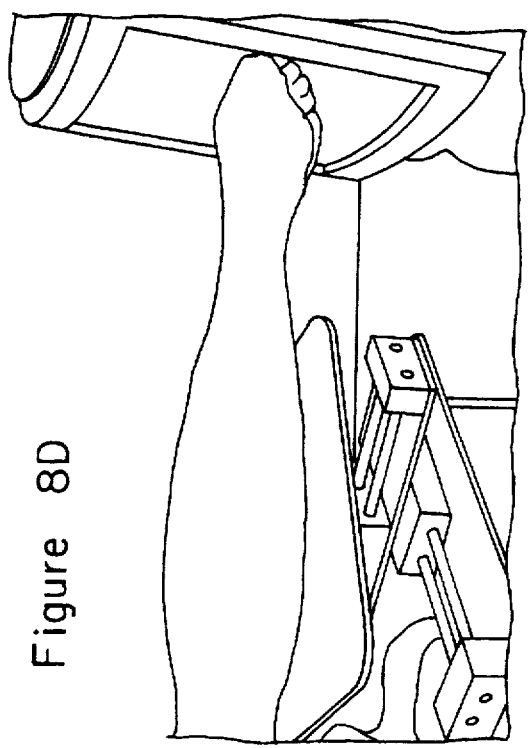
Figure 8E:
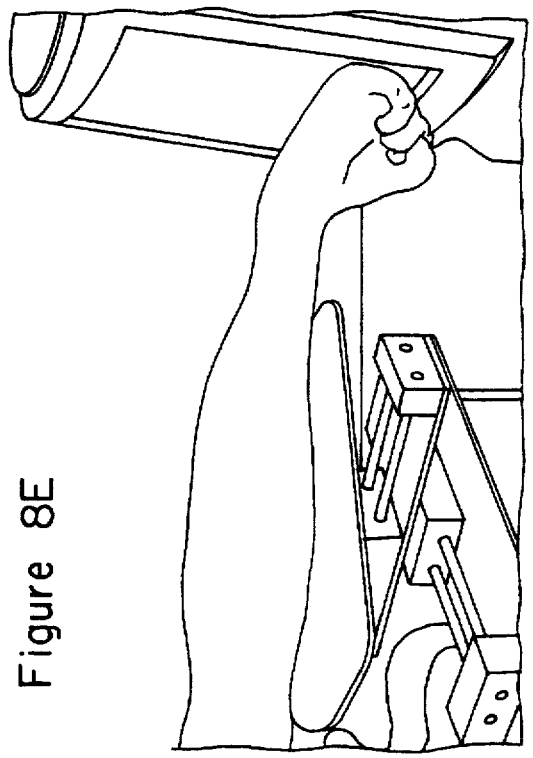
Figure 8F:
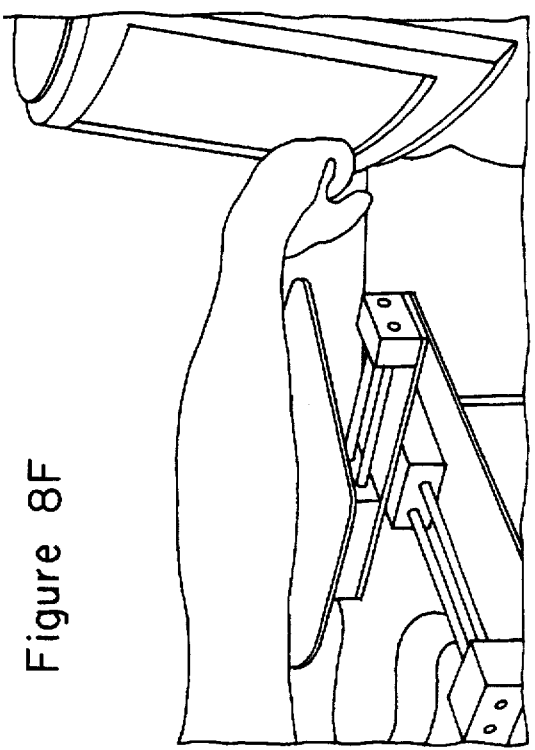
Figure 8G:
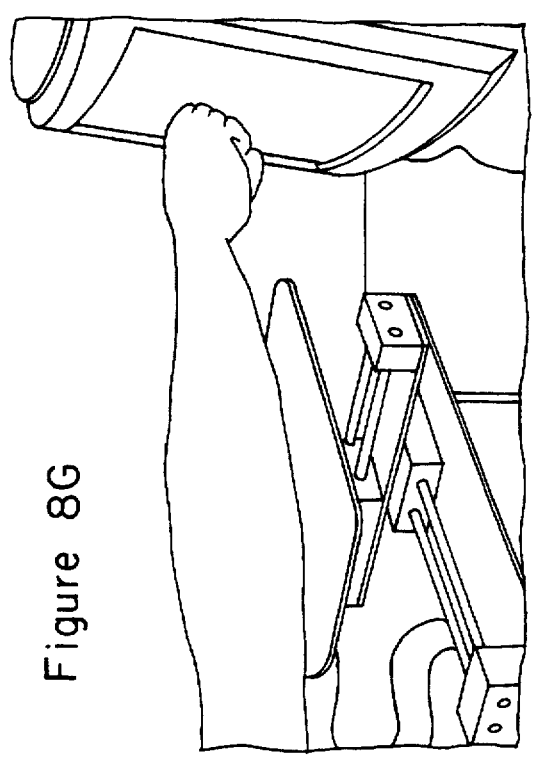
Figure 8H:
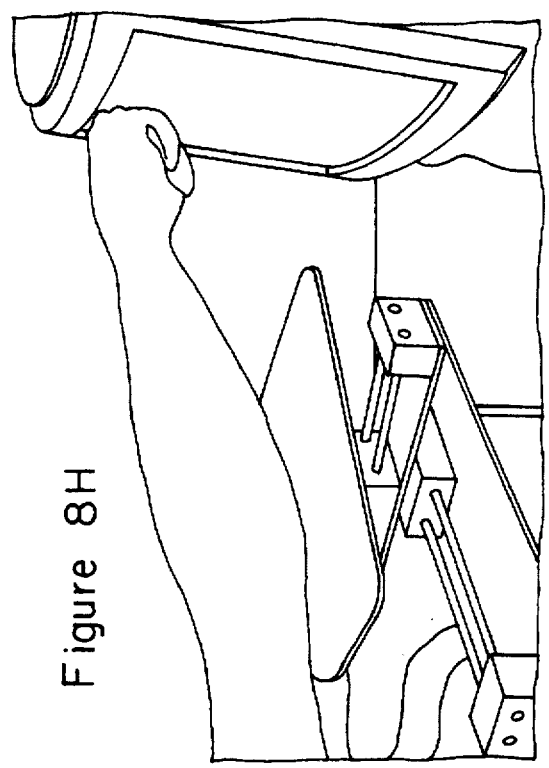
Figure 8J:
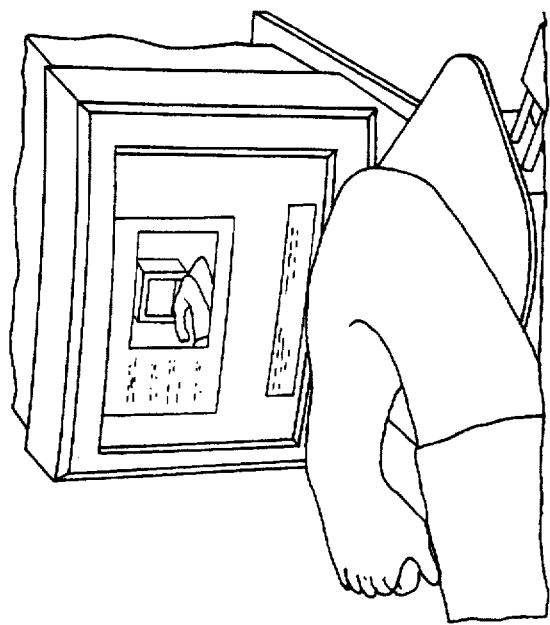
Figure 8I:
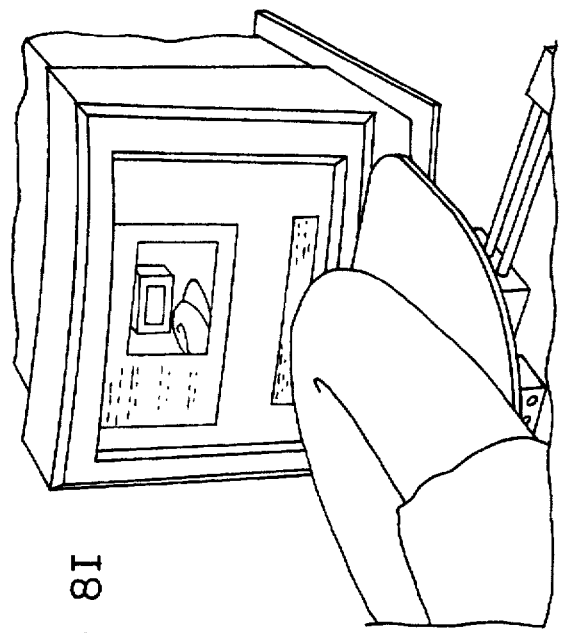
Figure 8K:
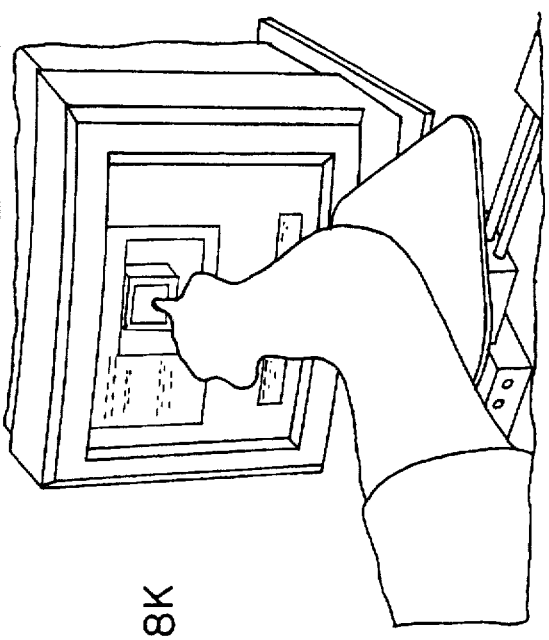

The arm movement actuator attachments 14 of the present invention advantageously provide an effective means to support the upper extremities of an individual having minimal mobility. To enable such an individual to interact with computer 16 through touch screen T, each actuator attachment 14 in use must satisfy various requirements. The first requirement is the need to maintain the individual's arm in the 'neutral position' which is defined herein as elevating and maintaining the arm so that at least the elbow and forearm of the seated individual are at chest level. This feature of the invention can be seen somewhat in FIGS. 8I–8K wherein it can be seen that the elbow and forearm are located in a generally horizontal plane at chest level of the seated individual. The second requirement of actuator attachment 14, while maintaining the arm in the neutral position, is the requirement of providing support directly beneath the elbow, as depicted in each of FIGS. 8A–8K. In this manner, resistance to the individual's tone is provided which allows the individual's arms to relax. Advantageously, therefore, the arm is prevented by the arm support platform 32 from sinking and inherently retracting into a fetal position. Failure to maintain the arm in the neutral position with proper elbow support, as provided herein through the present invention, also disadvantageously causes the individual to become distracted and lose their train of thought which compromises the rehabilitation program made possible through the system of this invention.

A third requirement of each actuator attachment 14 of the present invention is that, preferably, no straps or restraints of any type are used to secure the individual's arm to the support platform 32. It is essential for the individual to posture a number of times during the day and, during posturing, the individual's arms must be free to pull up and out away from the support platform 32. Providing positive restraint could cause injury.

Another important requirement relates to the minimum range of motion capabilities that must be provided with actuator attachments 14 in order to enable the individual to interact with the touch screen T without overreaching. Although it will be understood that the specific dimensions of the arm support platform 32 as well as the upper and lower slide rods 78,64 may be personally tailored to the needs of the individual, the following guidelines are preferably used in tailoring the dimensions of the actuator attachment components to the individual using the invention. All degree measurements assume that +0° is coincident with a vertical plane (Z-axis) extending forwardly from the individual in the longitudinal direction:

(1) The lower slide rail assembly 33 (X-axis) which allows left and right movement of the individual's arm should be long enough to allow full travel of the arm from a position of −30°−+30°.

(2) The upper slide assembly 34 (Y-axis) should allow outward and inward movement of the arm in forward and rearward directions so as to allow full travel of the arm from a fully drawn back position at 180° to a fully extended position at 0°.

(3) The moveable arm support platform 32 should be capable of full rotation through 360° about its vertical axis of rotation to thereby allow the individual's arm to bend from a position of −30°−+90° when built as a left side support 17, or from a position of −90°−+30° when built as a right side support 17.

(4) The individual's arm must be free to bend along the Z-axis (vertical or upward direction) from a position of +0° (i.e., flat on the platform 32) through +135° (i.e., up to the individual's shoulder). In other words, there should be no limitation on upward bending or movement placed on the arm by the movement actuator 17.

In order to satisfy the foregoing objectives, there exists certain resistance requirements that must be built into the assemblies of arm movement actuators 17. For example, in the X direction, left and right hand movement provided by the lower slide assembly 33 should occur with substantially 0% resistance; likewise, wide directional movement with the upper slide assembly 34 should also proceed with substantially 0% resistance both forward and backward. In the Z direction (up/down) there is preferably substantially 0% resistance in the up direction with 100% resistance in the down direction (i.e., below the plane of the arm support platform 32). Further, 100% resistance in the downward direction is necessary to provide appropriate resistance to tone. Furthermore, any device which is not effective to locate a support point directly beneath the individual's elbow is ineffective since it would fail to resist the individual's tone and would not be able to allow the individual's arm to be relaxed and thereby controlled by the individual. Substantially 0% resistance in the upward direction is necessary to avoid injury during posturing.

Accordingly, arm movement actuator attachment 17 of the invention has a number of advantages. An important advantage is the provision of an upper linear support connected to a wheelchair 12 that will be able to withstand a wide range of use and abuse while enabling the disabled individual to maximize minimal mobility in their upper extremities. The feature of providing a wide range of virtually frictionless movement within a horizontal plane by directly supporting both the individual's forearm and elbow enables the individual to achieve a computer assisted means of communication and perhaps to eventually relearn the skill of verbal communication. This is achieved by virtue of preventing the individual's arms from pulling down and back into a fetal position while enhancing the individual's ability to concentrate on the physical manipulation and mobilization of their upper extremity in an effort to engage a touch screen T that generates an input signal to a computer 16 running appropriate software for transmission of an audible or visual message 40 to enable communication.

In order to successfully teach an individual suffering traumatic brain injury the skill of communication through a computer assisted means of communication, it is necessary to teach the individual to increase their range of motion in their upper extremities which is followed by learning to bend the elbow, thereby allowing the upper arm to both straighten out and pull back as a result of the elbow's ability to bend. As a result of experimentation, the present inventor has discovered that this progression of relearning physical movement requires the use of a support device which directly supports the elbow. Once the elbow is able to bend, the impaired individual can then begin to use their shoulder to push their arm forward and pull it back again. Thus, the actuators 17 of the present invention provide an effective and unique means which enables such individuals to increase the mobility of their upper extremities.

FIGS. 8A–8K are perspective view illustrations to depict the manner in which attachment 14 of the invention and particularly armrest 20 thereon is manipulated so that the user's hand can touch various portions of a vertically disposed touch screen T such as may be found in a CRT.

An exemplary computer system 16, software 40 and touch screen T that may be used with actuator attachments 17 within the overall system of the invention will now be readily identifiable to one of ordinary skill in the art from a review of this specification.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

I claim:

1. A system for rehabilitating an individual suffering from a speech impairment, comprising:
   a. a platform having an upwardly facing surface for directly supporting at least an elbow and a forearm of said individual;
   b. a touch screen;
   c. a computer connected to said touch screen, said computer including communication software which generates at least one of visually and audibly detectable information corresponding to indicia on said touch screen to enable said individual to communicate with third parties;

further comprising moving means, connected to a support surface, for permitting movement of said platform in X and Y coordinate directions of a plane of movement in response to movement of said individual's arm.

2. The system of claim 1, wherein said platform is connected to a wheelchair.

3. The system of claim 2, wherein said moving means includes juxtaposed, upper and lower slide assemblies respectively moveable in one of said X and Y coordinate directions.

4. The system of claim 3, wherein said platform is rotatably mounted to the upper slide assembly.

5. The system of claim 3, wherein one end of the lower slide assembly is supported on an arm rest of said wheelchair and the opposite end of said lower slide assembly, cantilevered relative to said arm rest, is supported with an upright member projecting upwardly from a table top surface attached to said wheelchair.

6. An attachment for a wheelchair or the like of the type having an armrest structure on each side thereof, comprising:

a. a platform having an upwardly facing surface dimensioned for directly supporting at least an elbow and a forearm of an individual seated in the wheelchair; and b. moving means, connected to a support surface on the wheelchair, for permitting rectilinear movement of said platform in only X and Y coordinate directions defining a plane of movement in response to movement of said individual's arm and bending of said elbow on said platform.

7. The attachment of claim 6, wherein said moving means includes juxtaposed, upper and lower slide assemblies respectively moveable in one of said X and Y coordinate directions.

8. The attachment of claim 7, wherein said platform is rotatably mounted to the upper slide assembly.

9. The attachment of claim 8, wherein one end of the lower slide assembly is supported on an arm rest of said wheelchair and the opposite end of said lower slide assembly, cantilevered relative to said arm rest, is supported with an upright member projecting upwardly from a table top surface attached to said wheelchair.

10. A method of rehabilitating an individual confined to a wheelchair and having minimal mobility in their upper extremities, comprising the steps of:

a. placing the forearm and elbow of at least one of the arms of said individual on a moveable upwardly facing support surface which is capable of movement along two orthogonal coordinate axes while remaining at the same height; and b. teaching said individual to bend the elbow which is directly supported on said platform in order to move said platform.

11. The method of claim 10, comprising the further step of instructing the individual to physically contact a touch screen placed before said individual as a result of moving said platform and the individual's hand in accordance with step (b); and generating at least one of a visually and audibly detectable piece of information corresponding to indicia on said touch screen to enable said individual to communicate with third parties.

12. A method of rehabilitating an individual confined to a wheelchair and having minimal mobility in their upper extremities, comprising the steps of:

a. placing the forearm and elbow of at least one of the arms of said individual on a moveable upwardly facing support surface which is capable of movement along two orthogonal coordinate axes;

b. teaching said individual to bend the elbow which is directly supported on said platform in order to move said platform, and instructing the individual to physically contact a touch screen placed before said individual as a result of moving said platform and the individual's hand; and c. generating at least one of a visually and audibly detectable piece of information corresponding to indicia on said touch screen to enable said individual to communicate with third parties.

* * * * *